United States Patent [19]

Holroyd et al.

[11] Patent Number: 5,176,032
[45] Date of Patent: Jan. 5, 1993

[54] METHOD AND APPARATUS FOR PROCESSING ELECTRICAL SIGNALS AND A STRESS WAVE SENSOR

[75] Inventors: Trevor J. Holroyd; Timothy E. Tracey; Simon D. King; Neil Randall, all of Derby, England

[73] Assignee: Stresswave Technology Limited, Derby, England

[21] Appl. No.: 892,639

[22] Filed: Jun. 2, 1992

Related U.S. Application Data

[63] Continuation of Ser. No. 647,560, Jan. 29, 1991, abandoned.

[30] Foreign Application Priority Data

Feb. 21, 1990 [GB] United Kingdom ............... 9003878

[51] Int. Cl.$^5$ ........................................... G01N 29/14
[52] U.S. Cl. ..................................... 73/587; 340/683; 73/590
[58] Field of Search ................. 73/587, 590, 592, 593, 73/645, 646, 801; 340/683

[56] References Cited

U.S. PATENT DOCUMENTS

| 3,588,695 | 6/1991 | Furfaro | 324/111 |
| 3,677,072 | 7/1972 | Weichbrodt et al. | 340/683 |
| 4,086,816 | 5/1978 | Jon et al. | 73/587 |
| 4,207,771 | 6/1980 | Carlos et al. | 73/587 |
| 4,429,578 | 2/1984 | Darrel et al. | 340/683 |
| 4,459,850 | 7/1984 | Hyanova et al. | 73/587 |
| 4,942,387 | 7/1990 | Thomas | 73/660 |
| 5,005,415 | 4/1991 | Holroyd | 73/587 |

FOREIGN PATENT DOCUMENTS 0079260 5/1985 Japan ........................ 73/587

OTHER PUBLICATIONS

Patent Abstracts of Japan vol. 7, No. (p-168)(1155) Jan. 14, 1983.

Primary Examiner—Hezron E. Williams
Assistant Examiner—Rose M. Finley
Attorney, Agent, or Firm—Cushman, Darby & Cushman

[57] ABSTRACT

An apparatus for processing electrical signals corresponding to acoustic emissions produced in a machine or process comprises a transducer acoustically coupled to the machine or process, which detects the acoustic emissions and converts them into an output signal. The output signal is amplified by an amplifier, rectified and enveloped by an enveloper having a short time constant to produce an electrical signal. An enveloper having a long time constant, measures the mean level of the electrical signal. A DC component remover removes the DC component from the electrical signal and an enveloper, having a long time constant, measures the mean level of the rectified AC component of the electrical signal. A processor having a low sampling rate, measures a power of the ratio between the mean level of the rectified AC component of the electrical signal and the mean level of the electrical signal. The apparatus is self compensating for variations in the machine operating condition or transducer sensitivity and is relatively cheap to manufacture.

37 Claims, 4 Drawing Sheets

METHOD AND APPARATUS FOR PROCESSING ELECTRICAL SIGNALS AND A STRESS WAVE SENSOR

This is a continuation of application Ser. No. 07/647,560, filed on Jan. 29, 1991, which was abandoned upon the filing hereof.

present invention relates to a method and apparatus for processing electrical signals in order to recognise signal features indicative of variations in a process producing the electrical signals, and is particularly of interest for acoustic emissions or stress waves detected by transducers.

Acoustic emission or stress wave activity is associated with operating machinery or processes, and is produced as a result of friction, impacts, turbulence, cavitation, metal removal, crack growth or plastic deformation taking place during the operation of the machinery or process.

Acoustic emission techniques have been used to monitor the condition of machinery or processes, to assist in the detection and diagnosis of fault conditions sometimes at an early stage. The early detection of faults enables planned maintenance and replacement of degrading machinery or processes with a minimum of disruption and cost.

In prior art methods of processing acoustic emissions a transducer detects the acoustic emissions and produces an output signal, and the transducer output signal is processed to produce an electrical signal which corresponds to the acoustic emission activity. In a first prior art method the level of the electrical signal is measured, for example the mean level (RMS level). In this prior art method a fault is detected when there is a marked increase in the mean level of the electrical signal.

A good component operating under normal conditions gives a relatively low electrical signal level, corresponding to a relatively low acoustic emission activity whereas a bad component under normal conditions gives a relatively high electrical signal level, corresponding to a relatively high acoustic emission activity. A good component operating under adverse conditions also gives a relatively high electrical signal level. This method is therefore only suitable for use at a fixed operational condition or some method of normalising the electrical signal level measurement with respect to the operating conditions is required. Furthermore this type of measurement is sensitive to the detection sensitivity of the transducer during the measurement.

In a second method the ratio of the peak level of the electrical signal to the means level (RMS level) of the electrical signal is measured. The ratio of the peak level of the electrical signal to the mean of the electrical signal provides a measure of variations in the nature or form of the source processes producing the acoustic emissions enabling the occurrence of distress to be detected due to the increased occurrence of transient signal excursions. This method has the advantage of being self normalising since to a first approximation it is independent of the operating condition providing it remains at a similar level of distress and variations in signal detection sensitivity. A disadvantage of this method is the susceptibility of the measurement to spurious electrical noise signals such as those caused by electromagnetic switching transients, which can give rise to relatively high ratios of peak level of electrical signal to mean level of electrical signal.

In a third method, described in our copending European patent application 89310138.6 which claims priority from British patent application 8824793.7, the ratio of the mean level of the electrical signal to the minimum level of the electrical signal is measured. This method has the advantage of being self compensating for variations in the overall level of the electrical signal caused by variations in the operating conditions providing it remains at a similar level of distress or changes in transducer sensitivity. This method also has the advantage of not being significantly affected by electromagnetic switching transients as the mean level is only affected marginally and the minimum level is not affected. A disadvantage of this method is that the processor used to measure the mean level of the electrical signal has a high sampling rate to enable fast digitisation of the electrical signal level and consequently the processor is relatively expensive.

The present invention seeks to provide a method and apparatus for processing electrical signals in order to recognise signal features indicative of variations in the process producing them which overcomes the problems associated with the prior art methods and apparatus.

Accordingly the present invention provides a method of processing a varying electrical signal derived from an acoustic emission activity in order to recognise signal features indicative of variations in the process producing the varying electrical signal, comprises measuring the alternating current component of the electrical signal, and monitoring the measure of the alternating current component of the electrical signal for variations which are indicative of variations in the process producing the varying electrical signal.

Measuring and monitoring the alternating current component of the electrical signal enables earlier detection of faults in the process.

Preferably the mean value of the alternating current component of the electrical signal is measured.

The mean value of the electrical signal may be measured, a magnitude of the ratio between the measure of the alternating current component of the electrical signal and the mean of the electrical signal is measured, and the magnitude of the ratio is monitored for variations which are indicative of variations in the process producing the varying electrical signal.

This method is self compensating for variations in the overall level of the electrical signal level caused by variation in the operating conditions.

The ratio may be the mean value of the alternating current component of the electrical signal divided by the mean value of the electrical signal.

The electrical signal may correspond to the magnitude of the alternating current component of an output signal from a transducer corresponding to the acoustic emission activity generated by a process or a machine.

The electrical signal may correspond to the level of the acoustic emission activity.

The electrical signal may correspond to the intensity of the acoustic emission activity.

The electrical signal may correspond to a power of the level of the acoustic emission activity.

The electrical signal may correspond to the square of the level of the acoustic emission activity.

The present invention also provides an apparatus for processing a varying electrical signal derived from an acoustic emission activity in order to recognise features indicative of variations in the process producing the varying electrical signal characterized in that means measures the alternating current component of the electrical signal, and means to monitor the measure of the alternating current component of the electrical signal for variations which are indicative of variations in the process producing the varying electrical signal.

Preferably the means to measure the alternating current component of the electrical signal measures the mean value of the alternating current component of the electrical signal.

Means may measure the mean value of the electrical signal, means to determine a magnitude of the ratio between the measure of the alternating current component of the electrical signal and the mean value of the electrical signal, and means to monitor the magnitude of said ratio for variations which are indicative of variations in the process producing the varying electrical signal.

A divider means may determine the ratio of the mean value of the alternating current component of the electrical signal divided by the mean value of the electrical signal.

A first logarithmic amplifier means may produce the log of the mean value of the electrical signal, a second logarithmic amplifier means produces the log of the mean value of the alternating current component of the electrical signal subtractor means subtracts the log of the mean value of the electrical signal from the log of the mean value of the alternating current component of the electrical signal to determine the log of the ratio of the mean value of the alternating current component of the electrical signal to the mean value of the electrical signal.

At least one transducer may be acoustically coupled to the process producing acoustic emissions arranged to detect the acoustic emissions and processing means arranged to produce an electrical signal dependent upon the acoustic emission activity, the electrical signal corresponds to the magnitude of the alternating current component of an output signal from the transducer.

The electrical signal may correspond to the level of the acoustic emission activity.

The electrical signal may correspond to the intensity of the acoustic emission activity.

The electrical signal may correspond to a power of the level of the acoustic emission activity.

The electrical signal may correspond to the square of the level of the acoustic emission activity.

The means to determine the ratio may be arranged to operate an alarm when the ratio is equal to, greater than or less than a predetermined value.

The means to determine the ratio may be arranged to send a feedback signal to control the machine or process.

The means to measure the mean value of the alternating current component of the electrical signal may comprise an alternating current coupled enveloper with a relatively long time constant, and a rectifier.

The means to measure the mean value of the electrical signal may comprise an enveloper with a relatively long time constant.

The envelopers may have a 1 second time constant.

The processing means may comprise a rectifier and an enveloper having a relatively short time constant.

The enveloper may have a 100 microsecond time constant.

The present invention also provides a stress wave sensor comprising at least one transducer acoustically coupled to a process producing acoustic emissions, the transducer being arranged to detect the acoustic emissions and to produce an output signal, processor means being arranged to rectify and envelope the transducer output signal to produce an electrical signal characterized in that means measures the alternating current component of the electrical signal and means monitors the measure of the alternating current component of the electrical signal for variations which are indicative of variations in the process producing the acoustic emissions.

The means to measure the alternating current component of the electrical signal may measure the mean value of the alternating current component of the electrical signal.

The process may be an industrial process or machine.

Means may measure the mean value of the electrical signal, means to determine a magnitude of the ratio between the measure of the alternating current component of the electrical signal and the mean value of the electrical signal and means to monitor the magnitude of said ratio for variations which are indicative of variations in the process producing the acoustic emissions.

The present invention also provides a method of processing a varying electrical signal derived from an acoustic emission activity in order to recognise signal features indicative of variations in the process producing the varying electrical signal, comprising producing a slowly varying direct current representation of the alternating current component of the electrical signal and monitoring the slowly varying direct current representation of the alternating current component of the electrical signal for variations which are indicative of variations in the process producing the varying electrical signal.

A slowly varying direct current representation of the direct current component of the electrical signal may be produced, a magnitude of the ratio between the slowly varying direct current representation of the direct current component of the electrical signal and the slowly varying direct current representation of the direct current component of the electrical signal is determined and the magnitude of said ratio is monitored for variations which are indicative of variation in the process producing the varying electrical signal.

The present invention also provides a method of processing a varying electrical signal in order to recognise signal features indicative of variations in the process producing the varying electrical signal, comprising measuring the mean value of the alternating current component of the electrical signal and monitoring the mean value of the alternating current component of the electrical signal for variations which are indicative of variations in the process producing the varying electrical signal.

The mean value of the electrical signal may be measured, a magnitude of the ration between the mean value of the alternating current component of the electrical signal and the mean value of the electrical signal is determined and the magnitude of said ratio is monitored for variations which are indicative of variations in the process producing the varying electrical signal.

The present invention will be more fully described by way of example with reference to the accompanying drawings, in which.

Figure 1:
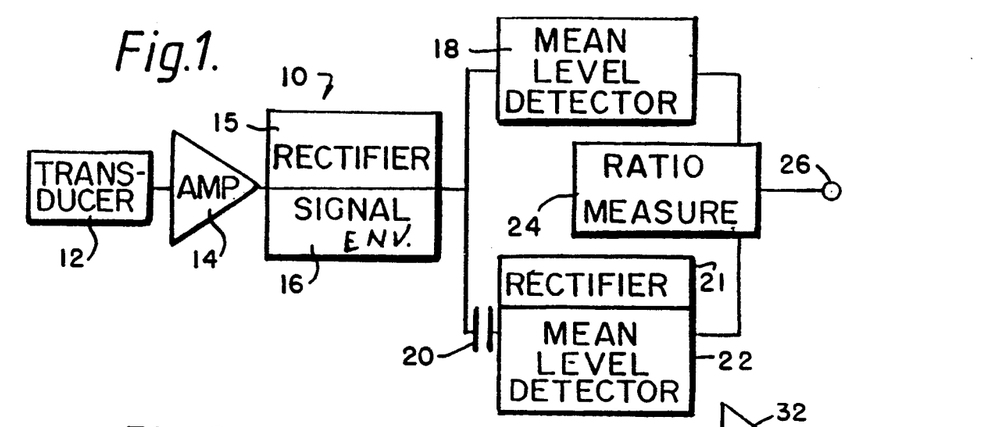
FIG. 1 is an apparatus for processing acoustic emissions according to the present invention.

An apparatus 10 for processing acoustic emissions to recognise features indicative of variations in the process producing the acoustic emissions is shown in FIG. 1. The apparatus 10 comprises a transducer 12 which is acoustically coupled to a source process of acoustic emissions. The transducer 12 is coupled to a machine, an industrial process or other structure in which acoustic emissions, stress waves or vibrations are generated as a result of the operation of the machine, industrial process or other reasons in the structure. The acoustic emissions are commonly generated as a result of frictional processes and impacts. The transducer 12 is arranged to detect the acoustic emissions generated by or in the machine, industrial process or structure and to produce an output signal dependent upon the acoustic emission activity detected. The transducer 12 is commonly a piezoceramic element, although other suitable types of transducer may be used, more than one transducer may be used.

The output signal produced by the transducer 12 is supplied to an amplifier 14. The amplifier 14 amplifies the output signal and may incorporate filters to select the required frequency band or frequency bands. The amplified output signal is rectified by a rectifier 15 and then supplied to a signal enveloper 16 which envelopes the rectified output signal. As an example the enveloper 16 envelopes the rectified output signal with a 100 micro second time constant, although other suitable time constants may be selected which allow variations in the electrical signal to be detected, and produces a varying electrical signal.

The varying electrical signal from the enveloper 16, e.g. the enveloped rectified output signal is supplied in parallel to a mean level detector 18, and to a DC component remover 20, a rectifier 21 and a mean level detector 22 arranged in series. The mean level detector 18 measures the mean, or average, level of the electrical signal. The mean level detector 18 provides a slowly varying DC representation of the DC component of the electrical signal. For example the mean level detector 18 is an enveloper which has a 1 second time constant and this integrates the electrical signal level over the measuring time period. Other suitable time constants may be used which produce slowly varying signals. The DC component remover 20 removes the DC component from the electrical signal to leave an AC component of the electrical signal. The AC component of the electrical signal is rectified by the rectifier 21 before passing to the mean level detector 22. The mean level detector 22 measures the mean level of the fluctuations of the rectified AC component of the electrical signal. The mean level detector 22 provides a slowly varying DC representation of the AC component of the electrical signal. For example the mean level detector 22 is an enveloper which also has a 1 second time constant and this integrates the fluctuations in the rectified AC component of the electrical signal over the measuring time period. Other suitable time constants may be used which provide slowly varying signals.

The mean level of the electrical signal as detected by the mean level detector 18 and the mean level of the rectified AC component of the electrical signal as detected by the mean level detector 22 are supplied to a ratio measurer 24. The ratio measurer 24 determines the ratio of the mean level of the rectified AC component of the electrical signal to the mean level of the electrical signal. The ratio measurer 24 divides the mean level of the rectified AC component of the electrical signal by the mean level of the electrical signal and supplies the output to an output terminal 26. The ratio measurer is a processor or a microprocessor with a low sampling rate.

The output terminal 26 may be connected to a display to show the ratio or may be connected to an alarm such that when the magnitude of the ratio reaches a predetermined value the alarm is operated, or may be connected to a control device such that the control device sends a feedback signal to control the operation of the machine or process, for example to adjust the amount of lubrication, or to stop the machine.

Figures 2, 3:
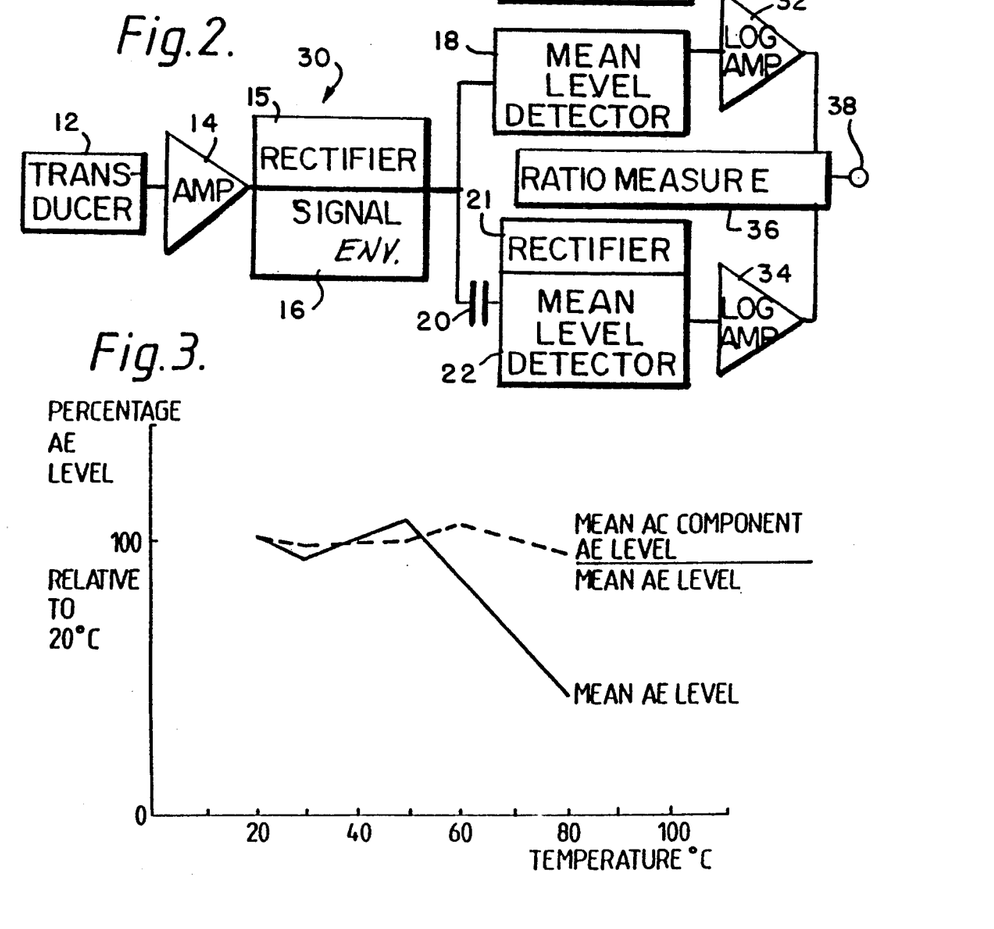
FIG. 2 is a second embodiment of an apparatus for processing acoustic emissions according to the present invention.
FIG. 3 is a graph of the acoustic emission level relative to the value at 20° against temperature.

FIG. 3 shows the relative acoustic emission level compared to that at 20° C. for various temperatures. The acoustic emission level detected by the transducer decreases with temperature due to changes in the sensitivity of the transducer with temperatures. The graph shows that a prior art device which measures the mean acoustic emission level will also suffer an apparent loss in acoustic emission level due to a decrease in sensitivity of the transducer caused by a temperature increase. The graph also shows that the ratio between the mean of the rectified AC component of the acoustic emission level and the mean acoustic emission level value remains substantially constant with temperature changes even though the transducer sensitivity changes. The ratio between the mean level of the rectified AC component of the acoustic emission level and the mean acoustic emission level also compensates for changes in transducer sensitivity due to other effects for example changes in acoustic coupling or damping characteristics of the sensor or machine.

Figure 4:
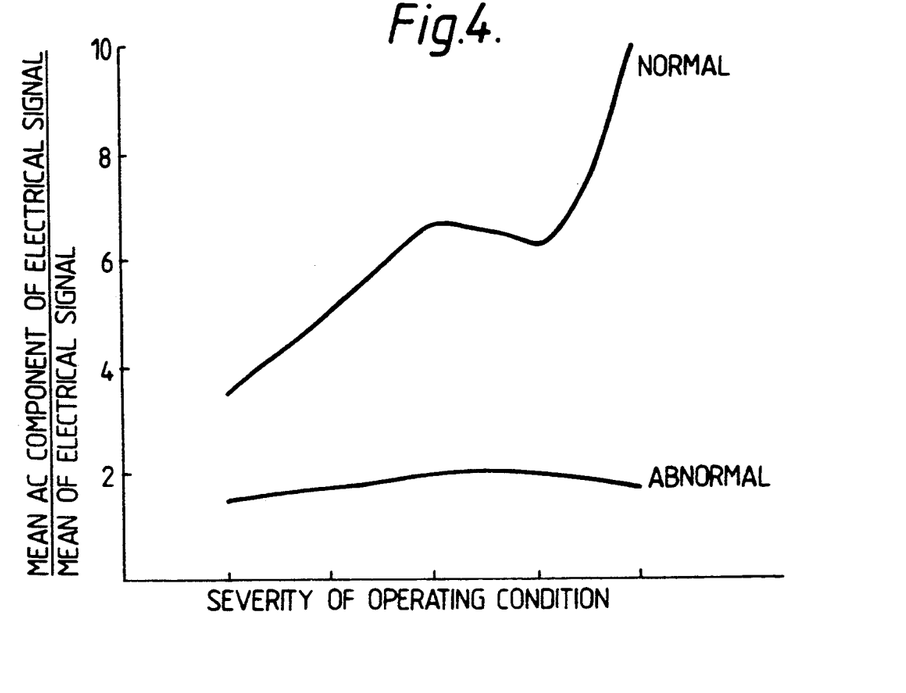
FIG. 4 is a graph of the ratio between the mean of the alternating current component of the electrical signal level and the mean signal level against operating condition.

FIG. 4 shows the effect on the ratio between the mean of the rectified AC component of the electrical signal level and the mean electrical signal level with varying operating conditions of a machine or industrial process for a normal and an abnormal machine or process. In this example for a normal machine or industrial process the ratio increases considerably with severity of the operating conditions, indicating an increase of distress, and we believe this to be characteristic in the early stages of degradation of the machine or process. For the abnormal condition, in the later stages of degradation of the machine or process, a lower value of the ratio is exhibited at all operating conditions, and we believe this to be a characteristic of degradation.

Figure 5:
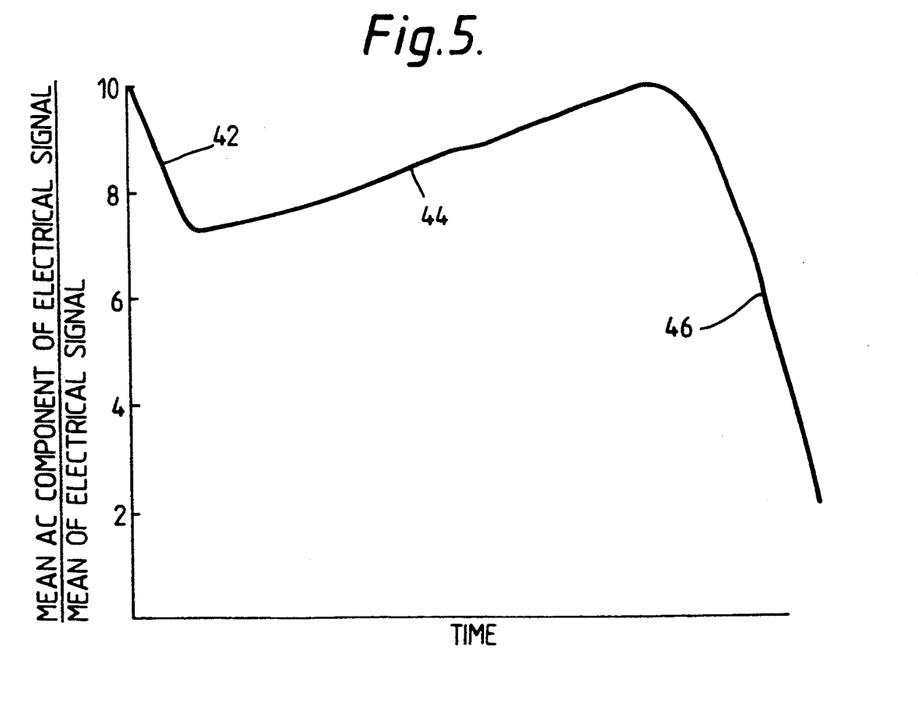
FIG. 5 is a graph of the ratio between the mean of the alternating current component of the electrical signal level and the mean of the electrical signal level against time.

FIG. 5 shows what we believe to be the effect on the ratio between the mean of the rectified AC component of the electrical signal level and the mean electrical signal level at a particular operating condition over time with increasing distress. The area 42 of the graph corresponds to bedding in of the machine, area 44 corresponds to progressively increasing distress of the machine during its working life and area 46 corresponds to the later stages of degradation in the approach to failure of the machine.

This method has the advantages of the second and third methods discussed in the prior art of being self compensating for variations in the overall level of the electrical signal level such as those caused by variations in the operating conditions providing it remains at a similar level of distress of the machine or industrial process, or for variations in the transducer sensitivity.

This method has the advantage of the third method of not being significantly affected by electromagnetic switching transients.

This method also has the advantage of using processors or microprocessors to measure the ratio between the mean of the rectified AC component of the electrical signal level and the mean of the electrical signal level, which require relatively slow sampling rates and are consequently much cheaper.

The use of the enveloping circuits with relatively long time constants to measure the mean of the rectified AC component of the electrical signal level and the mean electrical signal level enable a processor or microprocessor with a low sampling rate to be used.

A further apparatus 30 for processing acoustic emissions, shown in FIG. 2, comprises a transducer 12 which is acoustically coupled to a source process of acoustic emissions. The transducer 12 is arranged to detect the acoustic emissions generated in a machine, industrial process or structure and to produce an output signal dependent upon the acoustic emission activity detected.

The output signal produced by the transducer 12 is supplied to an amplifier 14. The amplifier 14 amplifies the output signal and the amplified output signal is rectified by a rectifier 15 and supplied to a signal enveloper 16. The enveloper 16 envelopes the rectified output signal to produce an electrical signal which is supplied to a mean level detector 18, and to a DC component remover 20, a rectifier 21 and a mean level detector 22 arranged in series. The mean level detector 18 measures the mean level of the electrical signal. The DC component remover 20 removes the DC component from the electrical signal to leave the AC component of electrical signal, and this is rectified by the rectifier 21. The mean level detector 22 measures the mean level of the fluctuations of the rectified AC component of the electrical signal.

The mean level of the electrical signal is supplied to a logarithmic amplifier 32 which produces an output signal which is the log of the mean level of the electrical signal. The mean level of the rectified AC component of the electrical signal is supplied to a logarithmic amplifier 34 which produces an output signal which is the log of the mean level of the rectified AC component of the electrical signal.

The output signals from the two logarithmic amplifiers 32 and 34 are supplied to a ratio measurer 36 which measures the ratio between the mean level of the rectified AC component of the electrical signal and the mean level of the electrical signal. The ratio measurer 36 is a subtracting amplifier and subtracts the output of one logarithmic amplifier from the other logarithmic amplifier, and produces an output proportional to the log of the ratio.

Figure 6:
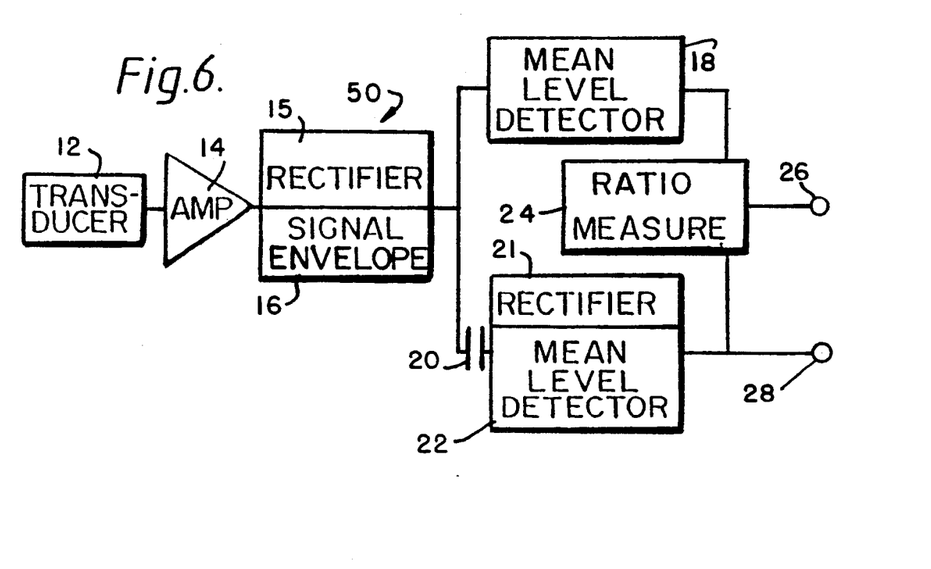
FIG. 6 is a third embodiment of an apparatus for processing acoustic emissions according to the present invention.

A further apparatus 50 for processing acoustic emissions, shown in FIG. 6, comprises a transducer 12 which is acoustically coupled to a source process of acoustic emissions. The transducer 12 is arranged to detect the acoustic emissions generated in a machine, industrial process or structure and to produce an output signal dependent upon the acoustic emission activity detected.

The output signal produced by the transducer 12 is supplied to an amplifier 14. The amplifier 14 amplifies the output signal and the amplified output signal is rectified by a rectifier 15 and supplied to a signal enveloper 16. The enveloper 16 envelopes the rectified output signal to produce an electrical signal which is supplied to a mean level detector 18, and to a DC component remover 20, a rectifier 21 and a mean level detector 22 arranged in series. The mean level detector 18 measures the mean level of the electrical signal. The DC component remover removes the DC component from the electrical signal to leave the AC component of the electrical signal, and this is rectified by the rectifier 21. The mean level detector 22 measure the mean level of the fluctuations of the rectified AC component of the electrical signal.

The mean level of the electrical signal as detected by the mean level detector 18 and the mean level of the rectified AC component of the electrical signal as detected by the mean level detector 22 are supplied to a ratio measurer 24. The ratio measurer 24 determines the ratio of the mean level of the rectified AC component of the electrical signal to the mean level of the electrical signal and supplies the output to an output terminal 26. Alternatively the mean level of the rectified AC component of the electrical signal as detected by the mean level detector 22 is supplied to a second output terminal 28.

The output terminal 26 may be connected to a display to show the ratio, or may be connected to an alarm such that when the ratio reaches a predetermined value the alarm is operated, or may be connected to a control device such that the control device sends a feedback signal to control the operation of the machine or process.

The output terminal 28 may be connected to a display to show the mean level of the rectified AC component of the electrical signal, or may be connected to an alarm such that when the mean level of the rectified AC component of the electrical signal reaches a predetermined value the alarm is operated, or may be connected to a control device such that the control device sends a feedback signal to control the operation of the machine or process.

Figure 7:
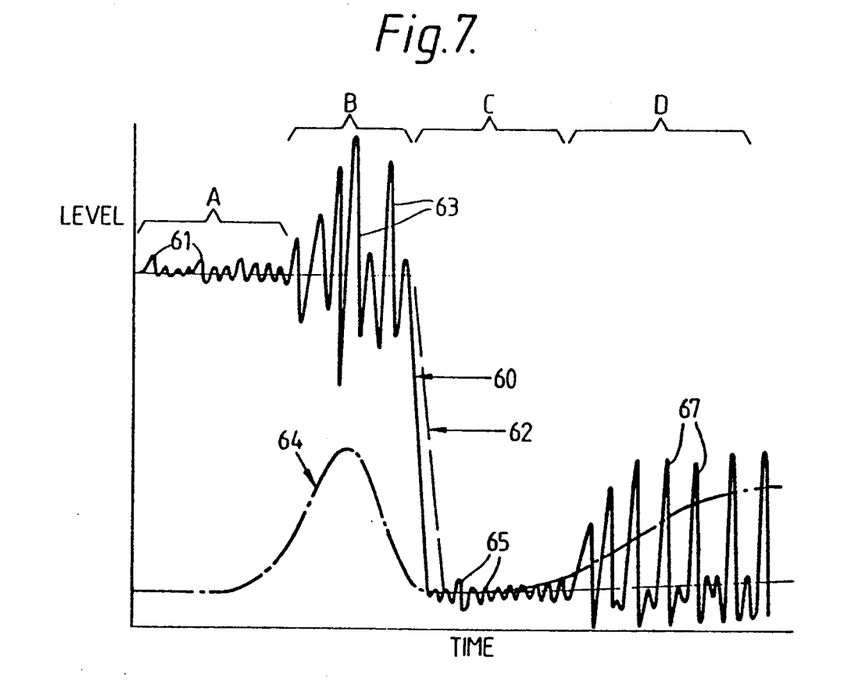
FIG. 7 is a graph comparing the electrical signal level, the mean of the alternating current component of the electrical signal level and the ratio between the mean of the alternating current component of the electrical signal level and the mean of the electrical signal level.

FIG. 7 shows an example of the varying electrical signal 60 produced by the enveloper 16, the corresponding mean level of the electrical signal 62 measured by the detector 18 and the corresponding mean level of the rectified AC component of the electrical signal 64 as measured by the detector 22. In region A the electrical signal 60 is at a relatively high level and is substantially constant i.e. the fluctuations 61 in the level are relatively small. The mean level of the electrical signal 62 is also relatively high, but the mean level of the rectified AC component of the electrical signal 64 is relatively low because the electrical signal 60 is substantially constant and has small fluctuations 61. In region B the electrical signal 60 is again at a relatively high level and is not constant i.e. the fluctuations 63 in the level are relatively high. The mean level of the electrical signal 62 is again relatively high and is unaffected by the fluctuations 63, but the mean level of the rectified AC component of the electrical signal 64 increases as the size and number of fluctuations 63 increases. In region C the electrical signal 60 is at a relatively low level and is substantially constant i.e. the fluctuations 65 in the level are relatively small. The mean level of the electrical signal 62 is also relatively low, and the mean level of the rectified AC component of the electrical signal 64 is relatively low because the electrical signal 60 is substantially constant and has small fluctuations 65. In region D the electrical signal 60 is at a relatively low level and is not constant i.e. the fluctuations 67 in the level are relatively high. The mean level of the electrical signal 62 is also relatively low, but the mean level of the AC component of the electrical signal 64 increases as the size and number of fluctuations 67 increases.

Figure 8:
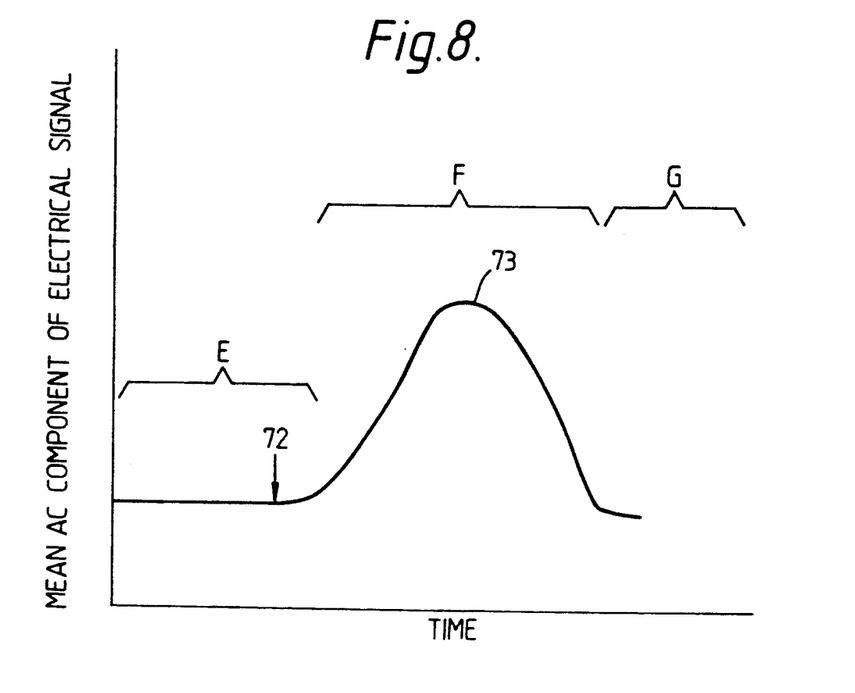
FIG. 8 is a graph of the mean of the alternating current component of the electrical signal level with time.
Figure 9:
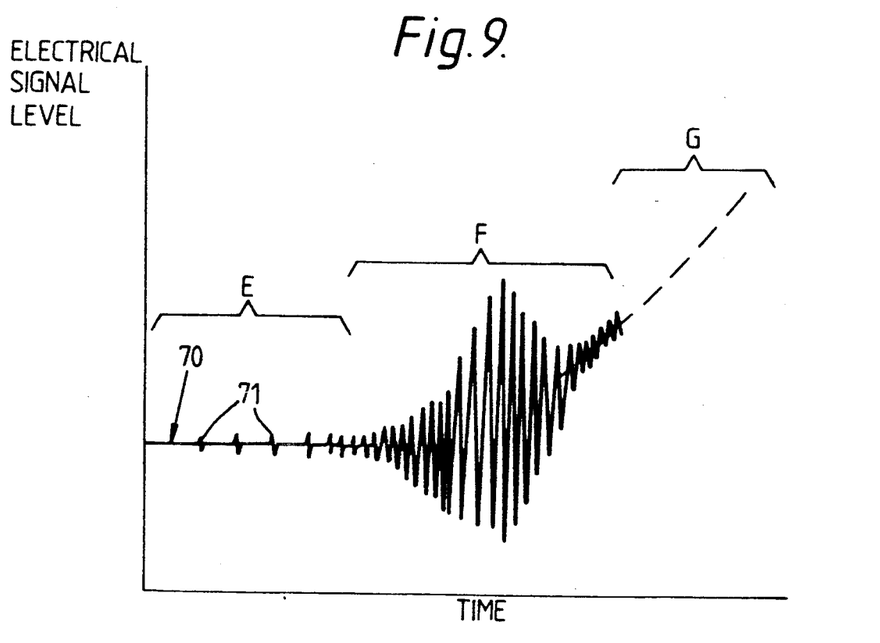
FIG. 9 is a graph of the electrical signal level against time.

FIGS. 8 and 9 show what we believe to be the affect on the mean level of the rectified AC component of the electrical signal at a particular operating condition with time with increasing distress. The electrical signal level 70 in FIG. 9 remains substantially uniform for a period of time in region E, and during this period the size and number of fluctuations 71 in the level of the electrical signal 70 are relatively low. Over the same time period E, as shown in FIG. 8, the mean level of the rectified AC component of the electrical signal 72 remains substantially uniform and relatively low. Region E corresponds to normal operation of a machine or process. The regions F and G of FIGS. 8 and 9 correspond to progressively increasing distress of the machine or process during its working life. In region F the electrical signal level 70 has increasing numbers of fluctuations 71 and the size of the fluctuations 71 increases to a maximum and then decreases. The fluctuations increase in size to a maximum and then decrease because the fluctuations produce a gradual increase in the constant/mean electrical signal level which effectively reduces the size of the fluctuations 71 from the constant/mean electrical signal level. In region F the mean level of the rectified AC component of the electrical signal 72 increases to a peak 73, corresponding to the maximum size of the fluctuations 71 in the electrical signal 70, and then decreases. It can be seen that the mean level of the rectified alternating current component of the electrical signal gives an early indication of increasing distress of the machine, or process, to enable the earliest possible detection of faults in the machine or process. The mean level of the rectified alternating current component of the electrical signal responds to the individual bursts of acoustic emission activity which are associated with the first signs of wear or damage.

Although the description has referred to measuring the mean level of the alternating current component of the electrical signal any suitable measure of the alternating current component of the electrical signal may be used.

The measuring of the ratio between the mean level of the rectified AC component of the electrical signal and the mean level of the electrical signal may be by dividing the mean level of the rectified AC component of the electrical signal by the mean level of the electrical signal or by dividing the mean level of the electrical signal by the mean level of the rectified AC component of the electrical signal. It is also possible to use other exponential powers of the mean level of the AC component of the electrical signal divided by the mean level of the electrical signal, for example squared.

The description has referred to the electrical signal being rectified before enveloping, the electrical signal may be half wave rectified, or full wave rectified for the measuring of the ratio.

The electrical signal may correspond to the acoustic emission level, the acoustic emission level squared, or some other exponential power of the acoustic emission level, the acoustic emission intensity, an exponential power of the acoustic emission intensity or the RMS level.

If a DC coupled transducer is used the electrical signal may be used under certain circumstances without rectification.

We claim:

1. A method of processing an outlet signal from a transducer, the outlet signal from the transducer corresponding to an acoustic emission activity generated by a process, comprising filtering and enveloping the transducer output signal to produce an electrical signal, removing a direct current component from the electrical signal, measuring an alternating current component of the electrical signal for variations which are indicative of variations in the process producing the acoustic emission.

2. A method as claimed in claim 1, comprising measuring a mean value of the electrical signal, determining a magnitude of the ratio between the measure of the alternating current component of the electrical signal and the mean value of the electrical signal and monitoring the magnitude of said ratio for variations which are indicative of variations in the process producing the acoustic emission.

3. A method as claimed in claim 2 comprising measuring a mean value of the alternating current component of the electrical signal and in which the ratio is the mean value of the alternating current component of the electrical signal divided by the mean value of the electrical signal.

4. A method as claimed in claim 1 comprising measuring a mean value of the alternating current component of the electrical signal.

5. A method as claimed in claim 1 in which the electrical signal corresponds to the level of the acoustic emission activity.

6. A method as claimed in claim 1 in which the electrical signal corresponds to the intensity of the acoustic emission activity.

7. A method as claimed in claim 1 in which the electrical signal corresponds to the level of the acoustic emission activity raised to an exponential power.

8. A method as claimed in claim 7 in which the electrical signal corresponds to the square of the level of the acoustic emission activity.

9. A method of processing an output signal from a transducer, the output signal from the transducer corresponding to an acoustic emission activity generated by a process or a machine, comprising filtering and enveloping the transducer output signal to produce an electrical signal, removing a direct current component from the electrical signal, producing a slowly varying direct current representation of an altering current component of the electrical signal for variations which ate indicative of variations in the process producing the acoustic emission.

10. A method of producing a varying electrical signal derived from an acoustic emission activity in order to recognise signal features indicative of variations in the process producing the acoustic emission activity, comprising producing a slowly varying direct current representation of an alternating current component of the electrical signal, producing a slowly varying direct current representation of a direct current component of the electrical signal, determining a magnitude of the ratio between the slowly varying direct current representation of the altering current component of the electrical signal and the slowly varying direct current representation of the direct current component of the electrical signal and monitoring the magnitude of the ratio for variations which are indicative of variations in the process producing the acoustic emission activity.

11. An apparatus for processing an acoustic emission activity in order to recognise features indicative of variations on a process producing the acoustic emission comprising at least one transducer acoustically coupled to a source for producing the acoustic emission, the transducer being arranged to detect the acoustic emission and to produce an output signal dependent upon the acoustic emission activity, processor means being electrically connected to the transducer and being arranged to filter and envelope the transducer output signal to produce an electrical signal, means to remove a direct current component from the electrical signal and to measure an alternating current component of the electrical signal being electrically connected to the processor means, means to monitor the measure of the alternating current component of the electrical signal for variations which are indicative of variations in the process producing the acoustic emission.

12. An apparatus as claimed in claim 11 comprising means to measure a mean value of the electrical signal electrically connected to the processor means, means to determine a magnitude of the ration between the measure of the alternating current component of the electrical signal and the mean value of the electrical signal being electrically connected to the means to measure the mean value of the electrical signal and to the means to remove the direct current component from the electrical signal and to measure the alternating current component of the electrical signal, and means to monitor the magnitude of the ratio for variations which are indicative of variations in the process producing the acoustic emissions being electrically connected to the means to determine the ratio.

13. An apparatus as claimed in claim 11 in which the means to measure the alternating current component of the electrical signal comprises means to measure a mean value of the alternating current component of the electrical signal.

14. An apparatus as claimed in claim 12 in which divider means determine the ratio of a mean value of the alternating current component of the electrical signal divided by the mean value of the electrical signal.

15. An apparatus as claimed in claim 12 in which a first logarithmic amplifier means produces the log of the mean value of the electrical signal, a second logarithmic amplifier means produces the log of the mean value of a alternating current component of the electrical signal, subtractor means subtracts the log of the mean value of the electrical signal from the log of the mean value of the alternating current component of the electrical signal to determine the log of the ratio of the mean value of the alternating current component of the electrical signal to the mean value of the electrical signal.

16. An apparatus as claimed in claim 11 in which the electrical signal corresponds to the level of the acoustic emission activity.

17. An apparatus as claimed in claim 11 in which the electrical signal corresponds to the intensity of the acoustic emission activity.

18. An apparatus as claimed in claim 11 in which the electrical signal corresponds to a level of the acoustic emission activity raised to an exponential power.

19. An apparatus as claimed in claim 18 in which the electrical signal corresponds to the level of the acoustic emission activity raised to the second exponential power.

20. An apparatus as claimed in claim 12 in which the means to determine the ratio is arranged to operate an alarm when the ratio is equal to, greater than or less than a predetermined value.

21. An apparatus as claimed in claim 12 in which the means to determine the ratio is arranged to send a feedback signal to control a machine or process.

22. An apparatus for processing a varying electrical signal derived from an acoustic emission activity in order to recognise features indicative of variations in a process producing the acoustic emission activity, comprising means to measure a mean value of an alternating current component of the electrical signal, in which the means to measure the mean value of the alternating current component of the electrical signal comprises an alternating current coupled enveloper, the enveloper having a relatively long time constant, and a rectifier, and means to monitor the measure of the mean value of the alternating current component of the electrical signal for variations which are indicative of variations in the process producing the acoustic emission activity.

23. An apparatus as claimed in claim 11 in which the means to measure the mean value of the electrical signal comprises an enveloper having a relatively long time constant.

24. An apparatus as claimed in claim 22 in which the enveloper has a 1 second time constant.

25. An apparatus as claimed in claim 23 in which the enveloper has a 1 second time constant.

26. An apparatus as claimed in claim 11 in which the processing means comprises a rectifier, and an enveloper having a relatively short time constant.

27. An apparatus as claimed in claim 26 in which the enveloper has 100 microsecond time constant.

28. A stress wave sensor comprising at least one transducer acoustically coupled to a source for producing acoustic emissions, the transducer being arranged to detect the acoustic emissions and to produce an output signal, processor means being electrically connected to the transducer and being arranged to filter and enveloper the transducer output signal to produce an electrical signal, means to measure a mean value of the electrical signal being electrically connected to the processor means, means to remove a direct current component from the electrical signal and to measure an alternating current component of the electrical signal being electrically connected to the processor means, means to determine a magnitude of a ratio between the measure of the alternating current component of the electrical signal and the mean value of the electrical signal being electrically connected to the means to measure the mean value of the electrical signal and to the means to remove the direct current component from the electrical signal and to measure the alternating current component of the electrical signal, and means to monitor the magnitude of the ratio for variations which are indicative of variations in the process producing the acoustic emissions being electrically connected to the means to determine the magnitude of the ratio.

29. A stress wave sensor as claimed in claim 28, in which the enveloper of the processor means has a short time constant.

30. A stress wave sensor as claimed in claim 29, in which the enveloper has a 100 microsecond time constant.

31. A stress wave sensor as claimed in claim 28, in which the means to measure the alternating current component of the electrical signal measures a mean value of the alternating current component of the electrical signal.

32. A stress wave sensor as claimed in claim 31, in which the means to measure the mean value of the alternating current component of the electrical signal comprises an enveloper having a long time constant.

33. A stress wave sensor as claimed in claim 32, in which the enveloper has a one second time constant.

34. A stress wave sensor as claimed in claim 28, in which the means to measure the mean value of the electrical signal comprises an enveloper having a long time constant.

35. A stress wave sensor as claimed in claim 34, in which the enveloper has a one second time constant.

36. A stress wave sensor as claimed in claim 28, in which the process in an industrial process or a machine.

37. An apparatus as claimed in claim 11 comprising means to measure a mean value of the electrical signal electrically connected to the processor means, means to determine a magnitude of a ratio between the measure of the alternating current component of the electrical signal and the mean value of the electrical signal being electrically connected to the means to measure the mean value of the electrical signal and to the means to remove the direct current component from the electrical signal and to measure the alternating current component of the electrical signal, and means to monitor the magnitude of the ratio for variations which are indicative of variations in the process producing the acoustic emissions being electrically connected to the means to determine the ration, wherein the means to measure the alternating current component of the electrical signal comprises means to measure a mean value of the alternating current component of the electrical signal.

* * * * *